US010550273B2

(12) United States Patent
Lehmann

(10) Patent No.: US 10,550,273 B2
(45) Date of Patent: Feb. 4, 2020

(54) METHOD FOR DETERMINING THE TEMPERATURE IN A FLOW CHANNEL OF A GAS TURBINE AND MEASURING DEVICE

(71) Applicant: Rolls-Royce Deutschland Ltd & Co KG, Blankenfelde-Mahlow (DE)

(72) Inventor: Knut Lehmann, Koenigs Wusterhausen (DE)

(73) Assignee: Rolls-Royce Deutschland Ltd & Co KG, Blankenfelde-Mahlow (DE)

( * ) Notice: Subject to any disclaimer, the term of this patent is extended or adjusted under 35 U.S.C. 154(b) by 169 days.

(21) Appl. No.: 15/790,486

(22) Filed: Oct. 23, 2017

(65) Prior Publication Data

US 2018/0112085 A1 Apr. 26, 2018

(30) Foreign Application Priority Data

Oct. 25, 2016 (DE) .......... 10 2016 120 297

(51) Int. Cl.
*C09D 5/26* (2006.01)
*G01K 11/14* (2006.01)
(Continued)

(52) U.S. Cl.
CPC ............ *C09D 5/26* (2013.01); *G01K 3/04* (2013.01); *G01K 11/12* (2013.01); *G01K 11/14* (2013.01);
(Continued)

(58) Field of Classification Search
CPC .................................................. G01K 11/14
See application file for complete search history.

(56) References Cited

U.S. PATENT DOCUMENTS 4,629,335 A 12/1986 Eckstein et al.
7,404,925 B2 7/2008 Watson et al.
(Continued)

FOREIGN PATENT DOCUMENTS

CH 706959 A2 3/2014
DE 3217832 A1 11/1983
(Continued)

OTHER PUBLICATIONS

European Search Report dated Feb. 21, 2018 from counterpart EP App No. 17197043.7.
(Continued)

*Primary Examiner* — Clayton E. LaBalle
*Assistant Examiner* — Leon W Rhodes, Jr.
(74) *Attorney, Agent, or Firm* — Shuttleworth & Ingersoll, PLC; Timothy Klima

(57) ABSTRACT

A method for determining temperature in a flow channel of a gas turbine positioned on a testing bench includes: arranging at least one rod-shaped element provided with a thermal paint coating inside the flow channel; operating the gas turbine on the testing bench in a defined operating mode, wherein the thermal paint coating of the at least one rod-shaped element changes its color depending on the temperature that the thermal paint coating is exposed to; detecting the color distribution of the thermal paint coating of the at least one rod-shaped element; and determining the temperature that has been present in the flow channel along the at least one rod-shaped element in the defined operating mode based on the detected color distribution. Another embodiment relates to a measuring device having a rod-shaped element provided with a thermal paint coating.

20 Claims, 3 Drawing Sheets

(51) Int. Cl.
    *G01K 3/04*     (2006.01)
    *G01K 13/02*     (2006.01)
    *G01K 11/12*     (2006.01)
    *G01N 21/77*     (2006.01)

(52) U.S. Cl.
CPC .......... *G01K 13/02* (2013.01); *F05D 2260/80* (2013.01); *F05D 2270/80* (2013.01); *G01K 2013/024* (2013.01); *G01K 2205/00* (2013.01); *G01N 2021/7796* (2013.01)

(56) References Cited

U.S. PATENT DOCUMENTS

| | | | |
|---|---|---|---|
| 7,819,578 | B2 | 10/2010 | Coney et al. |
| 9,482,579 | B2 * | 11/2016 | Badami ................. G01J 5/0088 |
| 2008/0144699 | A1 | 6/2008 | Plevich et al. |
| 2014/0064325 | A1 | 3/2014 | Kirtley |
| 2014/0098836 | A1 * | 4/2014 | Bird ........................ C09D 5/26 374/137 |
| 2015/0204198 | A1 | 7/2015 | Harivel et al. |
| 2016/0047751 | A1 | 2/2016 | Pless et al. |

FOREIGN PATENT DOCUMENTS

| | | |
|---|---|---|
| DE | 3737502 A1 | 5/1988 |
| DE | 602004000146 T2 | 4/2006 |
| EP | 1927833 A2 | 6/2008 |
| EP | 2440895 A1 | 4/2012 |
| FR | 2995678 A1 | 3/2014 |
| JP | S54110884 A | 8/1979 |
| JP | 08015042 A * | 1/1996 |
| JP | 2010019624 A * | 1/2010 |
| KR | 101428893 B1 * | 8/2014 |
| WO | 2010142307 A1 | 12/2010 |
| WO | WO2012168117 A2 | 12/2012 |

OTHER PUBLICATIONS

German Search Report dated Jun. 9, 2017 for counterpart German Application No. 10 2016 120 297.5.
Canadian Search Report dated Jun. 29, 2018 for counterpart Canadian Patent Application No. 2,983,852.
Canadian Search Report dated Mar. 26, 2019 for counterpart Canadian Patent Application No. 2,983,852.

* cited by examiner

METHOD FOR DETERMINING THE TEMPERATURE IN A FLOW CHANNEL OF A GAS TURBINE AND MEASURING DEVICE

REFERENCE TO RELATED APPLICATION

This application claims priority to German Patent Application No. 10 2016 120 297.5 filed on Oct. 25, 2016, the entirety of which is incorporated by reference herein.

BACKGROUND

The invention relates to a method for determining the temperature in a flow channel of a gas turbine and a measuring device that is suitable for being used in such a method.

For measuring the temperature of the flow in the flow channel of a gas turbine positioned on a testing bench, in particular for measuring the temperature behind the combustion chamber or in the area of the high-pressure turbine, it is known to take gas samples and to analyze the sampled gas by means of one or multiple measuring probes that project into the flow channel. The composition of the gas depends on the temperature of the sampled gas, so that the temperature can be determined based on the composition of the gas.

Since the measuring probes have to be cooled, such an approach is relatively laborious. Also, there is the danger that the flow in the flow channel, which is to be measured, is disturbed due to the size of the measuring probes.

There is a need to provide a simple method for determining the temperature in a flow channel of a gas turbine that does not influence the flow, or does so only to a minimal extent. There is further a need for a measuring device for use in such a method.

SUMMARY

According to an aspect of the invention, a method for determining the temperature in a flow channel of a gas turbine positioned on a testing bench is provided, comprising the following steps:
  arranging at least one rod-shaped element that is provided with a thermal paint coating inside the flow channel,
  operating the gas turbine on the testing bench in a defined operating mode, wherein the thermal paint coating of the at least one rod-shaped element changes color depending on the temperature which the thermal paint coating is exposed to,
  detecting the color distribution of the thermal paint coating of the at least one rod-shaped element, and
  determining the temperature that was present in the flow channel along the at least one rod-shaped element in the defined operating mode based on the detected color distribution.

Aspects of the invention are based on the idea of using thermal paints for measuring the temperature of the flow in the flow channel of a gas turbine, and on providing at least one rod-shaped element provided with a thermal paint coating for this purpose. The thermal paint of the used thermal paint coating has the characteristic that it changes its color at temperatures as they are present in the operational state in which the measuring is carried out. Thus, the temperature can be determined along the rod-shaped element based on the thermal paint coating or the color gradient of the thermal paint coating. At the same time, by using an elongated rod-shaped element, it is ensured that the flow in the flow channel is disturbed by the measuring device only to a minimal extent.

What is referred to as thermal paints are paints that change their color depending on the temperature. This can take place in a reversible or in an irreversible manner. In the case of an irreversible color change that is provided according to one embodiment of the invention, the evaluation of the color gradient can be carried out at any time after a measuring procedure has been concluded. Here, in an irreversible color change, the final color of the thermal paint coating is determined by the highest temperature that the thermal paint coating had been exposed to during operation of the gas turbine. Accordingly, the highest occurring temperature is detected.

In a reversible color change, the color gradient has to be recorded, for example by means of a camera, after the operating mode to be measured has been reached.

What is referred to as a thermal paint coating is any coating that contains thermal paints and that covers the surface of the rod-shaped element. The thermal paint coating can for example be applied by being sprayed on or being applied in a bath. The thermal paint coating can cover the rod-shaped element along its entire surface, or alternatively form an elongated strip on the rod-shaped element.

Thermal paints that are suitable for temperature indication in an area of an engine are known. For example, U.S. Pat. No. 7,404,925 B2 describes the use of thermal paints for determining the temperature of structural components of a gas turbine in the development of a gas turbine. Further examples of thermal paints that are suitable for temperature indication in the area of the engine are the thermal paint KN 6 that is available from Thermal Paint Services, Inc. in 8245 Cichlid Way, San Diego, Calif. 92129, USA, which has a temperature-dependent color in a temperature range of between 158° C. and 1380° C., and the thermal paint MC470-9 that is available from LCR Hallcrest Ltd, Riverside Buildings, Dock Road, Connah's Quay, Flintshire, CH5 4DS, UK, that has a temperature-dependent color in the temperature range of between 470° C. and 1210° C.

Defined operational modes of the gas turbine at which measuring is performed are all operational states in which a gas turbine may be operated. In the case of an aircraft engine, a defined operating mode is for example present if the aircraft engine is operated on the testing bench according to the operational conditions during takeoff, cruise flight, descent, etc.

In one embodiment of the invention, it is provided that a rod-shaped element that is provided with a thermal paint coating is arranged inside the flow channel in a radially extending manner. Here, the temperature profile of the flow in the flow channel along the radial direction can be detected at a given circumferential position and a given axial position based on the color distribution. It can be provided that multiple rod-shaped elements are arranged at different circumferential positions and/or at different axial positions inside the flow channel.

In a further embodiment of the invention, it is provided that a plurality of rod-shaped elements that are provided with a thermal paint coating are arranged inside the flow channel respectively with a radial extension and at a distance to each other in the circumferential direction. At that, the rod-shaped elements form a one-dimensional grid. Based on the color distributions of the thermal paint coatings of the plurality of the rod-shaped elements, a two-dimensional temperature profile of the flow in the flow channel can be detected at a given axial position.

According to a further embodiment, the plurality of rod-shaped elements that are provided with a thermal paint coating and that are arranged inside the flow channel form a two-dimensional grid, with the rod-shaped elements extending inside of it in two different directions. Since in this embodiment the color distributions of the thermal paint coatings can be detected in two directions, a two-dimensional temperature profile of the flow in the flow channel can be detected with an even higher resolution at a given axial position.

The rod-shaped element that is provided with a thermal paint coating can for example be a solid ceramic rod. Alternatively, a wire that is provided with a thermal paint coating can be used as the rod-shaped element. It may be a tungsten wire, for example.

According to a further embodiment, the rod-shaped element comprises a circular cross section. Accordingly, as an example, the rod-shaped element may be a ceramic rod or a tungsten wire with a circular cross section.

In general, any element that has a length which is larger than its diameter by at least the factor 5, in particular by at least the factor 10, in particular by at least the factor 50, is referred to as being rod-shaped within the meaning of the present invention. The rod-shaped element can consist of rigid or a flexible material.

According to an exemplary embodiment, the rod-shaped element that is arranged inside the flow channel has a diameter that is between 0.2 mm and 5 mm, in particular between 0.5 mm and 2 mm. The smaller the diameter of the rod-shaped element, the smaller the degree of influence that the rod-shaped element has on the flow.

Moreover, the choice of the diameter of the rod-shaped element is determined by two considerations between which a compromise has to be found. Rod-shaped elements with a small diameter are advantageous with respect to reducing thermal conduction along the rod-shaped element and thus the associated slurring of the temperature information. Rod-shaped elements with a larger diameter are advantageous with respect to providing greater mechanical stability and rendering the detection of the color information of the thermal paints on the rod-shaped element easier.

In principle, the at least one rod-shaped element can be arranged at any position in the flow channel of a gas turbine for the purpose of temperature measurement. In embodiments of the invention, it is provided that the rod-shaped element provided with a thermal paint coating is arranged inside the main flow channel directly behind the combustion chamber of the gas turbine or behind a guide vane or a rotor blade of a turbine stage. In that location, temperatures of more than 1000° C., for example up to approximately 1200° C., are present, so that thermal paints that are active in that range with respect to their color are used.

For attaching the rod-shaped element in the main flow channel, it is provided according to one embodiment of the invention that the rod-shaped element is clamped at its two ends between a radially outer structure and a radially inner structure of the gas turbine which delimit the main flow path. For example, it can be provided that the rod-shaped element is clamped between an outer platform and an inner platform of a turbine guide vane segment of a turbine guide vane ring. In alternative embodiments, it is provided that the rod-shaped element is attached only at a radially outer structure, in particular a housing structure that delimits the main flow channel radially outside, or only at a radially inner structure that delimits the main flow channel radially inside. In this case, it projects into the main flow channel from a side.

According to a further aspect of the invention, the invention relates to a measuring device that has a rod-shaped element which provided with a thermal paint coating.

At that, the choice of the thermal paint depends on the application site or the temperatures that are present at the same in the operational state that is to be measured. For example, the thermal paint coating can be provided and embodied for the purpose of changing its color at temperatures that occur at the exit of the combustion chamber in the main flow path of a gas turbine, or of changing its color at temperatures that occur in the turbine, in particular the high-pressure turbine, in the main flow path of a gas turbine.

The measuring device can have multiple rod-shaped elements that form a one-dimensional grid or a two-dimensional grid.

As has already been mentioned, it is provided in one embodiment of the invention that the thermal paint coating is irreversible in the sense that its color is determined by the highest temperature that the thermal paint coating is exposed to. Thus, the highest temperatures that it is exposed to during operation on the testing bench are, as it were, imprinted on the rod-shaped element with respect to its color along its longitudinal extension. Thus, a stationary color profile is created that encodes a stationary temperature profile through its color distribution.

BRIEF DESCRIPTION OF THE DRAWINGS

The invention will be explained in more detail on the basis of exemplary embodiments with reference to the accompanying drawings in which.

DETAILED DESCRIPTION

Figure 1:
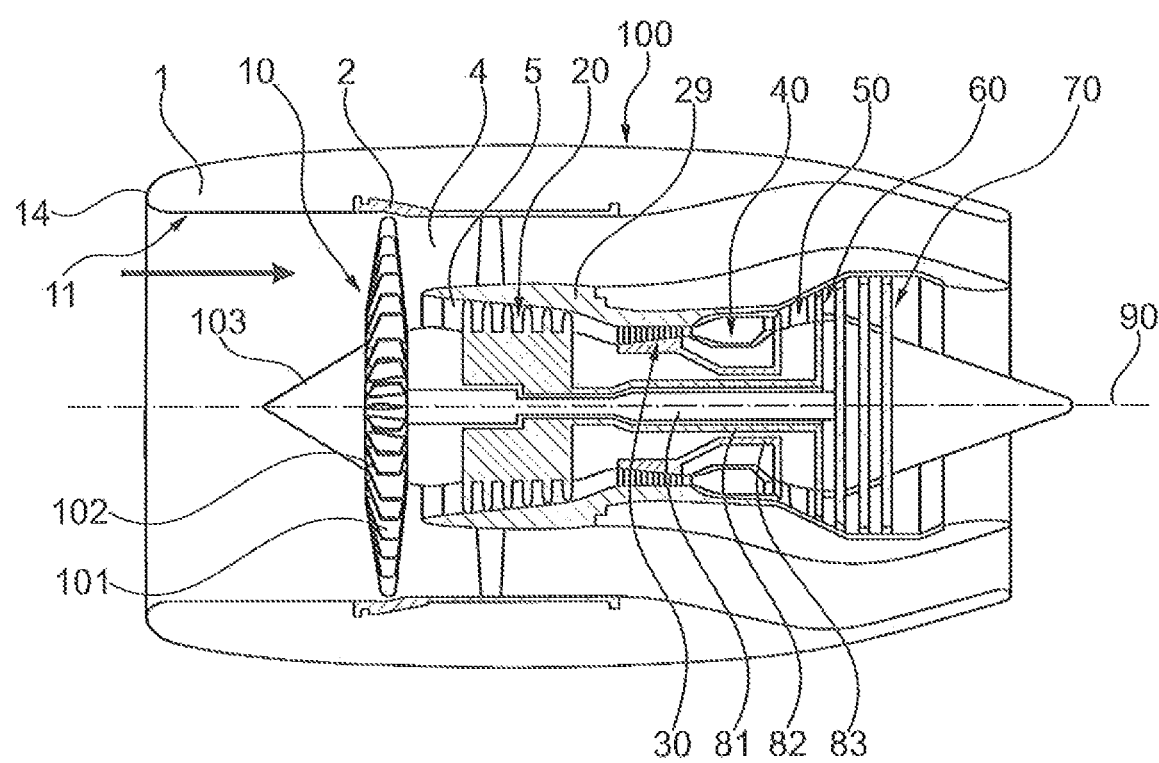
FIG. 1 shows a simplified schematic sectional view of a turbofan engine in which the present invention can be realized.

FIG. 1 shows, in a schematic manner, a turbofan engine 100 that has a fan stage with a fan 10 as the low-pressure compressor, a medium-pressure compressor 20, a high-pressure compressor 30, a combustion chamber 40, a high-pressure turbine 50, a medium-pressure turbine 60, and a low-pressure turbine 70.

The medium-pressure compressor 20 and the high-pressure compressor 30 respectively have a plurality of compressor stages that respectively comprise a rotor stage and a stator stage. The turbofan engine 100 of FIG. 1 further has three separate shafts, a low-pressure shaft 81 that connects the low-pressure turbine 70 to the fan 10, a medium-pressure shaft 82 that connects the medium-pressure turbine 60 to the medium-pressure compressor 20, and a high-pressure shaft 83 that connects the high-pressure turbine 50 to the high-pressure compressor 30. However, this is to be understood to be merely an example. If, for example, the turbofan engine has no medium-pressure compressor and no medium-pressure turbine, only a low-pressure shaft and a high-pressure shaft would be present.

The turbofan engine 100 has an engine nacelle 1 that comprises an inlet lip 14 and forms an engine inlet 11 at the inner side, supplying inflowing air to the fan 10. The fan 10 has a plurality of fan blades 101 that are connected to a fan disk 102. Here, the annulus of the fan disk 102 forms the radially inner boundary of the flow path through the fan 10. Radially outside, the flow path is delimited by the fan housing 2. Upstream of the fan-disc 102, a nose cone 103 is arranged.

Behind the fan 10, the turbofan engine 100 forms a secondary flow channel 4 and a primary flow channel 5. The primary flow channel 5 leads through the core engine (gas turbine) that comprises the medium-pressure compressor 20, the high-pressure compressor 30, the combustion chamber 40, the high-pressure turbine 50, the medium-pressure turbine 60, and the low-pressure turbine 70. At that, the medium-pressure compressor 20 and the high-pressure compressor 30 are surrounded by a circumferential housing 29 which forms an annulus surface at the internal side, delimitating the primary flow channel 5 radially outside. Radially inside, the primary flow channel 5 is delimited by corresponding rim surfaces of the rotors and stators of the respective compressor stages, or by the hub or by elements of the corresponding drive shaft connected to the hub.

During operation of the turbofan engine 100, a primary flow flows through the primary flow channel 5 (also referred to as the main flow channel in the following). The secondary flow channel 4, which is also referred to as the partial-flow channel, sheath flow channel, or bypass channel, guides air sucked in by the fan 10 during operation of the turbofan engine 100 past the core engine.

The described components have a common symmetry axis 90. The symmetry axis 90 defines an axial direction of the turbofan engine. A radial direction of the turbofan engine extends perpendicularly to the axial direction.

What is regarded in the context of the present invention is the situation that the turbofan engine 100 or a different aircraft engine or a gas turbine is positioned on a testing bench, with the temperature being measured in the main flow channel.

For temperature measurement, at least one rod-shaped element that is provided with a thermal paint coating is arranged inside the main flow channel. After the rod-shaped element has been placed in the area in which the temperature measurement is to be carried out, the turbofan engine is operated on the testing bench in a defined mode. At that, the thermal paint coating of the rod-shaped element changes its color depending on the temperature that the thermal paint coating is exposed to. Based on the color distribution of the thermal paint coating, the temperature that had been present in the main flow channel along the rod-shaped element in the defined operating mode is determined. There is an unambiguous relation between the color and the temperature.

Figure 2:
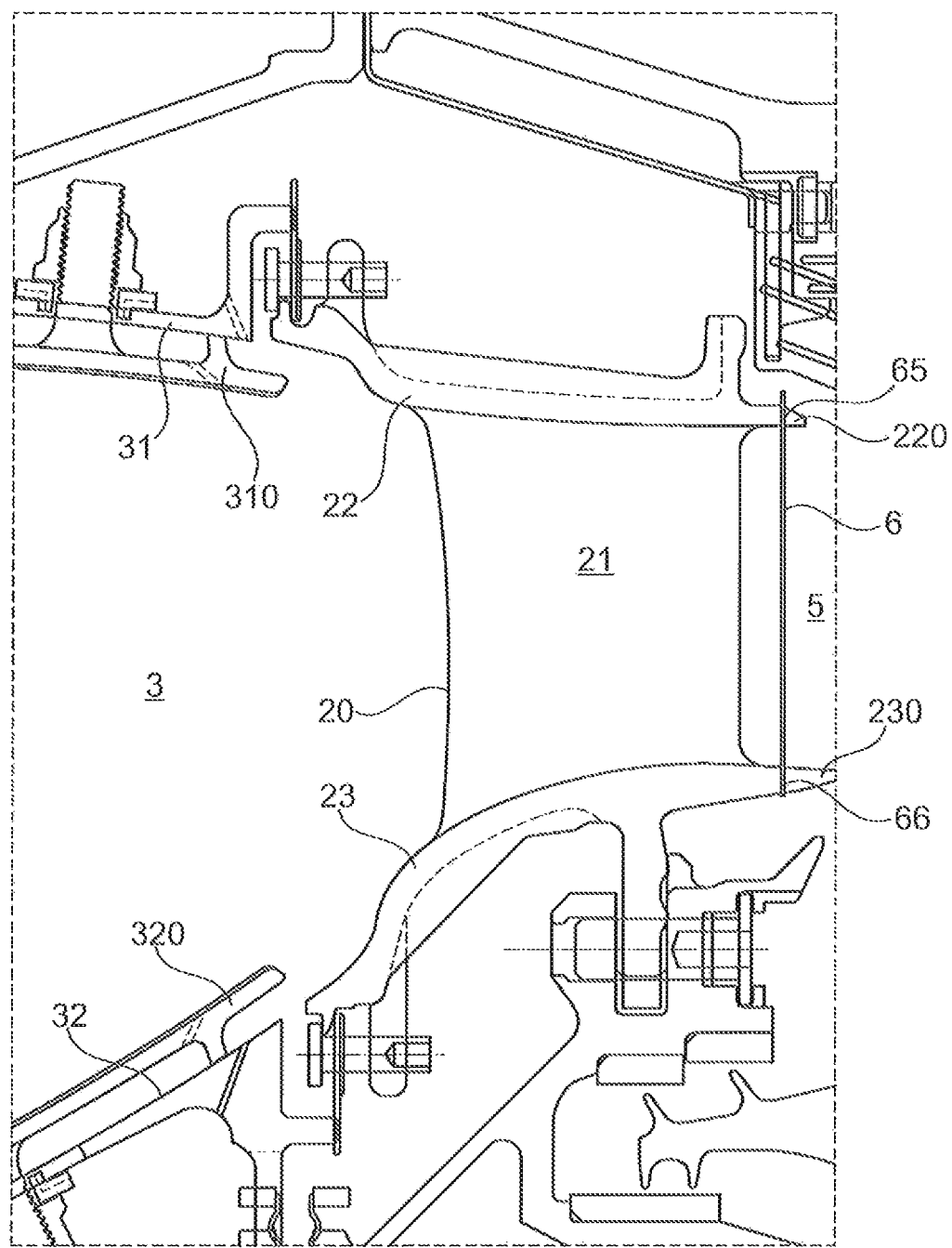
FIG. 2 shows a partial section of the main flow channel of a turbofan engine, wherein the opening of the combustion chamber and a turbine guide vane segment of stage 1 of a high-pressure compressor adjacent thereto are shown, and wherein a rod-shaped element that is provided with a thermal paint coating is arranged in the flow direction behind the turbine guide vane segment inside the main flow channel.

For example, according to FIG. 2, a temperature measurement is carried out behind the first guide vane ring of a high-pressure turbine that is arranged behind the combustion chamber. FIG. 2 shows a combustion chamber 3 that comprises a radially outer combustion chamber wall 31 and a radially inner combustion chamber wall 32. The combustion chamber walls 31, 32 are clad with heat shingles 310, 320. Located in the flow direction directly behind the exit of the combustion chamber 3 is a guide vane ring that consists of a plurality of guide vane segments 20 which are arranged next to each other in the circumferential direction, together forming the guide vane ring.

Each guide vane segment 20 comprises one or multiple guide vanes 21, an outer platform 22, and an inner platform 23.

For temperature measurement, a rod-shaped element 6 is used that extends in the radial direction through the main flow channel 5. For attaching the rod-shaped element 6, the outer platform 22 respectively has a bore or the like at its downstream end 220, and the inner platform 23 respectively has a bore or the like at its downstream end 230, with the bore receiving the ends 65, 66 of the rod-shaped element 6 and affixing the same.

Figure 3:
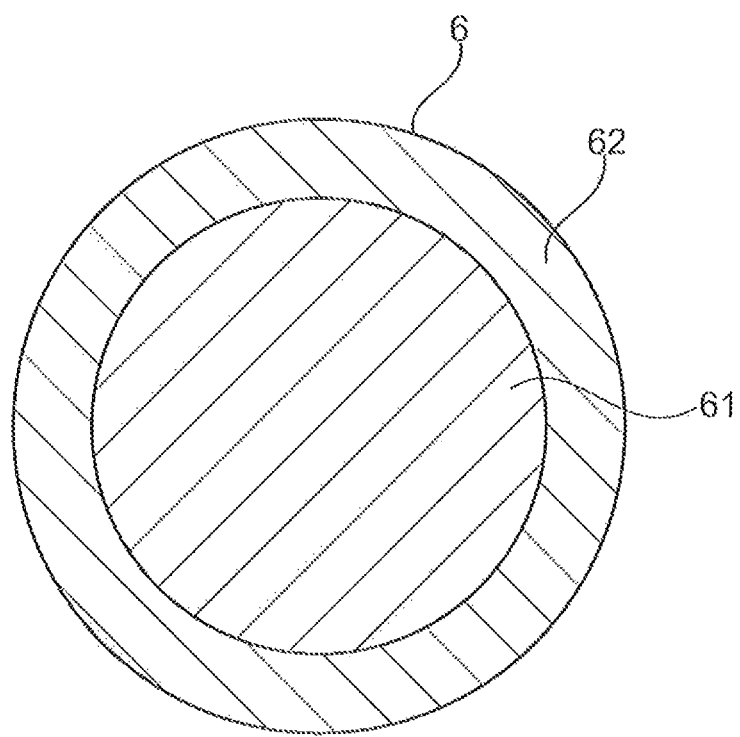
FIG. 3 shows a cross-sectional view of a rod-shaped element that is provided with a thermal paint coating.

According to FIG. 3, the rod-shaped element 6 consists of a rod-shaped core 61 which is coated with a thermal paint coating 62 which contains the thermal paints. The thermal paint coating 62 has been provided by being sprayed on or by the rod-shaped core 61 being submerged in a bath with thermal paints. The circular cross-sectional shape of the rod-shaped element 6 shown in FIG. 3 is to be understood to be merely an example. In principle, the rod-shaped element can have any desired cross-sectional shape.

The rod-shaped core 61 can for example be a solid ceramic rod that is heat-resistant at the occurring temperatures of more than 1000° C. For example, the solid ceramic rod can consist of a sintered high-grade $Al_2O_3$ ceramic material. A further suitable material is SSiC (sintered silicon carbide). The rod-shaped element 6 can for example have a diameter that is in the range of between 0.2 mm and 5 mm, in particular in the range of between 0.5 mm and 2 mm, including the coating.

The thermal paint coating 62 comprises thermal paints that take on a color depending on the temperature, at temperatures as they occur at the measurement site, in the regarded exemplary embodiment behind the first turbine guide vane ring. Typically, the temperatures that occur behind the first turbine guide vane ring are in the range of between 1000° C. and 1400° C., in particular in the range of between 1000° C. and 1200° C. At that, according to an exemplary embodiment, the used thermal paints are irreversible, i.e. they maintain their color as it has appeared at the highest temperature to which they have been exposed.

Thus, the temperature profile of the highest temperatures that occur at the measuring site can be directly determined based on the color profile along the ceramic rod 6 after the operation of the aircraft engine in the testing bench has been terminated. Here, the temperature profile along the radial direction can be determined at a certain circumferential position and a certain axial position in the main flow channel 5 by means of a single rod-shaped element 6.

If one or multiple rod-shaped elements 6 are provided at each guide vane segment 20 of the guide vane ring, the rod-shaped elements 6 form a one-dimensional grid, and a two-dimensional temperature profile of the flow in the main flow channel can be detected at the given axial position by means of the plurality of such rod-shaped elements.

It can also be provided that further rod-shaped elements are used, extending longitudinally in different directions, for example respectively from the outer platform 22 of a guide vane segment to an inner platform 23 of a guide vane segment that is adjacent thereto, so that in total a kind of cross grid is provided, whereby a two-dimensional temperature profile can be recorded even more precisely at the given axial position.

In an alternative exemplary embodiment, what is used as the rod-shaped core 61 is not a ceramic rod, but a tungsten wire coated with thermal paints.

The present invention is not limited in its embodiment to the previously described exemplary embodiments. For example, the site and type of the connection of the rod-shaped element at the radially outer and the radial inner boundary of the main flow channels are to be understood merely as an example.

It is furthermore pointed out that the features of the individually described exemplary embodiments of the invention can be combined in various combinations with one another. Where areas are defined, they include all the values within these areas and all the sub-areas falling within an area.

What is claimed is:

1. A method for determining a temperature in a flow channel of a gas turbine positioned on a testing bench, wherein the method comprises:
   providing at least one rod-shaped element with a thermal paint coating, wherein the at least one rod-shaped element is a solid ceramic rod;
   arranging the at least one rod-shaped element inside the flow channel;
   operating the gas turbine on the testing bench in a defined operating mode, wherein the thermal paint coating of the at least one rod-shaped element changes color depending on a temperature to which the thermal paint coating is exposed;
   detecting a color distribution of the thermal paint coating; and
   determining a temperature profile of a flow that had been present in the flow channel along the at least one rod-shaped element in the defined operating mode based on the color distribution of the thermal paint coating.

2. The method according to claim 1, wherein the at least one a rod-shaped element extends in a radial direction with respect to a rotational axis of the gas turbine inside the flow channel, and detecting the color distribution of the thermal paint coating along the radial direction at a given circumferential position and a given axial position with respect to the rotational axis of the gas turbine.

3. The method according to claim 1, further comprising:
   providing that the at least one rod-shaped element includes a plurality of rod-shaped elements;
   arranging the plurality of rod-shaped elements circumferentially inside the flow channel at a distance with respect to one another;
   detecting the color distribution of the thermal paint coating for each of the plurality of rod-shaped elements; and
   determining a two-dimensional temperature profile of the flow in the flow channel at a given axial position based on the color distribution of the thermal paint coating for each of the plurality of rod-shaped elements.

4. The method according to claim 1, further comprising:
   providing that the at least one rod-shaped element includes a plurality of rod-shaped elements to form a two-dimensional grid;
   arranging the two-dimensional grid inside the flow channel;
   detecting the color distributions of the thermal paint coatings of the plurality of rod-shaped elements; and
   determining the temperature profile of the flow based on the color distributions of the thermal paint coatings.

5. The method according to claim 1, wherein the at least one rod-shaped element has a diameter that is between 0.2 mm and 5 mm.

6. The method according to claim 1, wherein the at least one rod-shaped element is arranged behind a combustion chamber of the gas turbine inside the flow channel.

7. The method according to claim 1, wherein the at least one rod-shaped element is arranged behind at least one chosen from a guide vane and a rotor blade of a turbine stage of the gas turbine inside the flow channel.

8. The method according to claim 1, wherein the at least one rod-shaped element includes two ends, wherein a first end of the two ends is located at a radially inner end of the at least one rod-shaped element with respect to a radial direction of a rotational axis of the gas turbine, and a second end of the two ends is located at a radially outer end of the at least one rod-shaped element, wherein the at least one rod-shaped element is clamped at each of the two ends between a radially outer structure and a radially inner structure of the gas turbine which delimit the flow channel.

9. The method according to claim 8, further comprising providing a turbine guide vane segment of a turbine guide vane ring, wherein the turbine guide vane segment includes an outer platform and an inner platform, and wherein the radially outer structure is the outer platform and the radially inner structure is the inner platform.

10. The method according to claim 1, further comprising:
    providing that the color distribution of the thermal paint coating changes irreversibly depending on the temperature;
    determining a maximum temperature to which the thermal paint coating has been exposed during the defined operating mode of the gas turbine based on the color distribution; and
    recording the maximum temperature.

11. A method for determining a temperature in a flow channel of a gas turbine positioned on a testing bench, wherein the method comprises:
    providing at least one rod-shaped element with a thermal paint coating, wherein the at least one rod-shaped element is a solid ceramic rod;
    arranging the at least one rod-shaped element inside the flow channel, wherein the at least one rod-shaped element extends in a radial direction with respect to a rotational axis of the gas turbine;
    operating the gas turbine on the testing bench in a defined operating mode, wherein the thermal paint coating of the at least one rod-shaped element changes color depending on a temperature to which the thermal paint coating is exposed;
    detecting a color distribution of the thermal paint coating along the radial direction at a given circumferential position and a given axial position with respect to the rotational axis of the gas turbine; and
    determining a temperature profile of a flow that had been present in the flow channel along the at least one rod-shaped element in the defined operating mode based on the color distribution of the thermal paint coating.

12. A method for determining a temperature in a flow channel of a gas turbine positioned on a testing bench, wherein the method comprises:
    providing at least one rod-shaped element with a thermal paint coating;
    arranging the at least one rod-shaped element inside the flow channel, wherein the at least one rod-shaped element includes two ends, and wherein the at least one rod-shaped element is clamped at the two ends between a radially outer structure and a radially inner structure of the gas turbine which delimit the flow channel;
    operating the gas turbine on the testing bench in a defined operating mode, wherein the thermal paint coating of the at least one rod-shaped element changes color depending on a temperature to which the thermal paint coating is exposed;

detecting a color distribution of the thermal paint coating; and determining a temperature profile of a flow that had been present in the flow channel along the at least one rod-shaped element in the defined operating mode based on the color distribution of the thermal paint coating.

13. The method according to claim 12, providing the at least one a rod-shaped element extends in the radial direction inside the flow channel, and detecting the color distribution of the thermal paint coating along the radial direction at a given circumferential position and a given axial position with respect to the rotational axis of the gas turbine.

14. The method according to claim 12, further comprising:

providing that the at least one rod-shaped element includes a plurality of rod-shaped elements;

arranging the plurality of rod-shaped elements circumferentially inside the flow channel at a distance with respect to one another;

detecting the color distribution of the thermal paint coating for each of the plurality of rod-shaped elements; and determining a two-dimensional temperature profile of the flow in the flow channel at a given axial position based on the color distribution of the thermal paint coating for each of the plurality of rod-shaped elements.

15. The method according to claim 12, further comprising:

providing that the at least one rod-shaped element includes a plurality of rod-shaped elements to form a two-dimensional grid;

arranging the two-dimensional grid inside the flow channel;

detecting the color distributions of the thermal paint coatings of the plurality of rod-shaped elements; and determining the temperature profile of the flow based on the color distributions of the thermal paint coatings.

16. The method according to claim 12, wherein the at least one rod-shaped element is a wire.

17. The method according to claim 16, wherein the at least one rod-shaped element is a tungsten wire.

18. The method according to claim 12, wherein the at least one rod-shaped element is arranged behind a combustion chamber of the gas turbine inside the flow channel.

19. The method according to claim 12, wherein the at least one rod-shaped element is arranged behind at least one chosen from a guide vane and a rotor blade of a turbine stage of the gas turbine inside the flow channel.

20. The method according to claim 12, further comprising providing a turbine guide vane segment of a turbine guide vane ring, wherein the turbine guide vane segment includes an outer platform and an inner platform, and wherein the radially outer structure is the outer platform and the radially inner structure is the inner platform.

* * * * *